US012685703B2

(12) United States Patent
Kamei

(10) Patent No.: US 12,685,703 B2
(45) **Date of Patent: *Jul. 21, 2026**

(54) ORGANOPOLYSILOXANE-MODIFIED CYCLODEXTRIN COMPOUND AND COSMETICS CONTAINING SAME

(71) Applicant: Shin-Etsu Chemical Co., Ltd., Tokyo (JP)

(72) Inventor: Masanao Kamei, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 362 days.

This patent is subject to a terminal disclaimer.

(21) Appl. No.: 18/567,076

(22) PCT Filed: Jun. 3, 2022

(86) PCT No.: PCT/JP2022/022568

§ 371 (c)(1),
(2) Date: Dec. 5, 2023

(87) PCT Pub. No.: WO2022/259964

PCT Pub. Date: Dec. 15, 2022

(65) Prior Publication Data

US 2024/0261209 A1 Aug. 8, 2024

(30) Foreign Application Priority Data

Jun. 8, 2021 (JP) ................................ 2021-095979

(51) Int. Cl.
*A61K 8/73* (2006.01)
*A61Q 19/00* (2006.01)
*C07H 23/00* (2006.01)

(52) U.S. Cl.
CPC .............. *A61K 8/738* (2013.01); *A61Q 19/00* (2013.01); *C07H 23/00* (2013.01); *A61K 2800/10* (2013.01)

(58) Field of Classification Search
CPC ..................................................... A61K 8/738
See application file for complete search history.

(56) References Cited

U.S. PATENT DOCUMENTS 5,583,244 A 12/1996 Uchida et al.
2007/0015729 A1 1/2007 Geckeler et al.
2011/0200661 A1 8/2011 Alvarez Lorenzo et al.

FOREIGN PATENT DOCUMENTS

CN 105367985 A 3/2016
JP 6-145201 A 5/1994
JP 7-70204 A 3/1995
JP 8-134103 A 5/1996
JP 10-29910 A 2/1998
JP 2000-508010 A 6/2000

(Continued)

OTHER PUBLICATIONS

International Search Report (PCT/ISA/210), issued in PCT/JP2022/022568, dated Aug. 23, 2022.

(Continued)

*Primary Examiner* — Golam M Shameem

(74) *Attorney, Agent, or Firm* — Birch, Stewart, Kolasch & Birch, LLP

(57) ABSTRACT

This organopolysiloxane-modified cyclodextrin compound is composed of a sugar unit represented by formula (1)

(1)

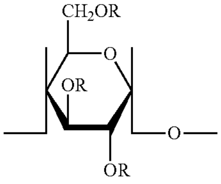

[in the formula, R is a hydrogen atom, a group represented by formula (2)

(2)

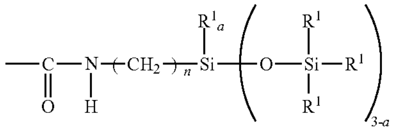

(in the formula, $R^1$ is a group selected from among a C1-C8 alkyl group, a C1-C8 fluorine-substituted alkyl group, and a C6-C12 aryl group, n is an integer of 1-10, and a is an integer of 0-3), or a group represented by formula (3)

(3)

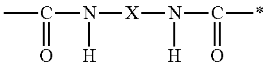

(in the formula, X is a divalent organic group, and * is a bond that is bonded to a hydroxyl group of another sugar unit)], wherein the ratio among the number $N_H$ of moles of the hydrogen atom, the number $N_S$ of moles of the group represented by formula (2), and the number $N_L$ of moles of the group represented by formula (3) satisfies $N_H$:$N_S$:$N_L$=0.5-2.5:0.3-2.0:0.1-0.5, and $N_H$+$N_S$+$N_L$ is 3.0.

9 Claims, No Drawings

(56) References Cited

FOREIGN PATENT DOCUMENTS

| | | | |
|---|---|---|---|
| JP | 2007-23280 | A | 2/2007 |
| JP | 2007-106789 | A | 4/2007 |
| JP | 2009-24094 | A | 2/2009 |
| JP | 2011-529998 | A | 12/2011 |
| JP | 2013-233473 | A | 11/2013 |
| JP | 2018-35306 | A | 3/2018 |

OTHER PUBLICATIONS

Written Opinion of the International Searching Authority (PCT/ISA/237), issued in PCT/JP2022/022568, dated Aug. 23, 2022.

ORGANOPOLYSILOXANE-MODIFIED CYCLODEXTRIN COMPOUND AND COSMETICS CONTAINING SAME

TECHNICAL FIELD

This invention relates to an organopolysiloxane-modified cyclodextrin compound and a cosmetic composition comprising the same.

BACKGROUND ART

Cyclodextrins have a doughnut structure composed of a lipophilic inside and a hydrophilic outside and having an inclusion ability to take active ingredients in the cavity. Since this enables to solubilize substantially insoluble substances to improve their stability in products, cyclodextrins are used in a wide variety of products including medicines, foods, cosmetics, textiles and paints. While cyclodextrins are often used as additives, polymers having cyclodextrin groups are also reported. For example, cyclodextrin condensed polymers are obtained by reacting cyclodextrins with diisocyanate compounds and utilized as a selective anchoring agent for halogenated aromatic compounds contained in organic media (see Patent Document 1). Also, derivatives having cyclodextrins bonded via an amide group are effective for improving the water solubility of substantially water insoluble compounds and their application to pharmaceuticals and cosmetics is reported (see Patent Documents 2 and 3).

Acrylic hydrogels having cyclodextrin on side chain have an ability to incorporate medical ingredients, active ingredients or protective agents and are used in contact lenses and cosmetics (see Patent Document 4). Also, cyclodextrin conjugates having a polyoxyethylene group as a linking spacer can include a variety of guest molecules (see Patent Document 5). It is noted that all these are intended to include various ingredients.

PRIOR ART DOCUMENTS

Patent Documents

Patent Document 1: JP-A 2013-233473
Patent Document 2: JP-A 2007-106789
Patent Document 3: JP-A 2009-024094
Patent Document 4: JP-A 2011-529998
Patent Document 5: JP-A 2007-023280

SUMMARY OF INVENTION

Technical Problem

An object of the invention is to provide an organopolysiloxane-modified cyclodextrin compound and a cosmetic composition comprising the same. The cyclodextrin compound is able to enhance the blending stability or age stability of oils, typically silicone oil, in cosmetics. A cosmetic composition having the cyclodextrin compound blended therein is effectively spreadable and free of greasy or sticky feel, gives a dry light feel characteristic of silicone oil. Since the cyclodextrin compound is effectively adhesive to the skin, it improves the lasting performance or retention of cosmetics. When a cosmetic composition further contains pharmaceutical, fragrant or other components, another object of the invention is to provide a cosmetic composition in which these components can be blended in a stable manner.

Solution to Problem

Making extensive investigations to attain the above objects, the inventor has found that the outstanding problem is solved when the ratio of substitution of hydrogen of three hydroxyl groups in sugar units of which an organopolysiloxane-modified cyclodextrin compound is composed, that is, the ratio of the molar number $N_H$ of hydrogen, the molar number $N_S$ of specific triorganosilyl-modified amide group, and the molar number $N_L$ of specific linking group having divalent urethane bond is in a specific range. The invention is predicated on this finding.

Accordingly, the invention provides an organopolysiloxane-modified cyclodextrin compound and a cosmetic composition comprising the same, as defined below.

1. An organopolysiloxane-modified cyclodextrin compound composed of sugar units having the formula (1):

[Chem. 1]

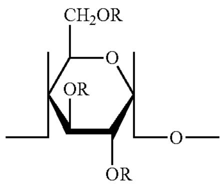

(1)

wherein R is independently hydrogen, a group having the formula (2):

[Chem. 2]

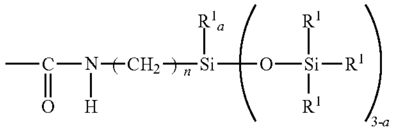

(2)

wherein $R^1$ is independently a group selected from among C1-C8 alkyl groups, C1-C8 fluorine-substituted alkyl groups, C6-C12 aryl groups, and C7-C12 aralkyl groups, n is an integer of 1 to 10, and a is an integer of 0 to 3, or a group having the formula (3):

[Chem. 3]

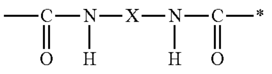

(3)

wherein X is a divalent organic group, and * is a point of attachment to a hydroxyl group of another sugar unit, wherein the ratio of the molar number $N_H$ of the hydrogen, the molar number $N_S$ of the group having formula (2), and the molar number $N_L$ of the group having formula (3) per mole of the organopolysiloxane-modified cyclodextrin compound is $N_H$:$N_S$:$N_L$=(0.5 to 2.5):(0.3 to 2.0):(0.1 to 0.5) and $N_H$+$N_S$+$N_L$=3.0.

2. The organopolysiloxane-modified cyclodextrin compound of 1 wherein X is a divalent organic group selected from C1-C10 divalent aliphatic hydrocarbon groups, C6-C20 divalent aromatic hydrocarbon groups, and groups having the formula (4):

[Chem. 4]

(4)

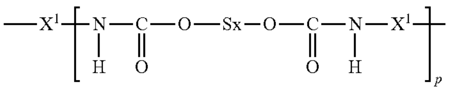

wherein $X^1$ is independently a C1-C10 divalent aliphatic hydrocarbon group or C6-C20 divalent aromatic hydrocarbon group, Sx is a divalent organopolysiloxane residue having the formula (5):

[Chem. 5]

(5)

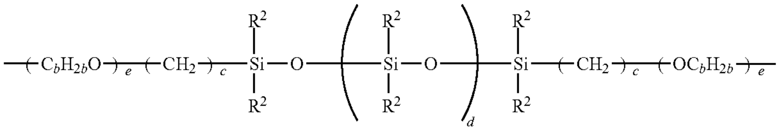

wherein $R^2$ is independently a group selected from among C1-C8 alkyl groups, C1-C8 fluorine-substituted alkyl groups, C6-C12 aryl groups, and C7-C12 aralkyl groups, b is independently a number of 2 to 4, c is independently an integer of 2 to 12, d is independently an integer of 0 to 200, e is independently a number of 0 to 40, and p is a number of 1 to 5.

3. The organopolysiloxane-modified cyclodextrin compound of 2 wherein X is a group selected from the following divalent hydrocarbon groups.

[Chem. 6]

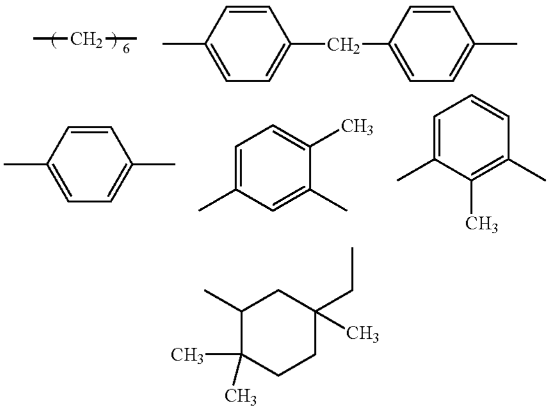

4. The organopolysiloxane-modified cyclodextrin compound of any one of 1 to 3 wherein the sugar unit having formula (1) is derived from a cyclodextrin compound selected from α-cyclodextrin, β-cyclodextrin, γ-cyclodextrin, and derivatives of the foregoing cyclodextrins having a hydroxyethyl or hydroxypropyl group.

5. The organopolysiloxane-modified cyclodextrin compound of any one of 1 to 4 wherein in formula (2), n=3 and $R^1$ is methyl.

6. A cosmetic composition comprising the organopolysiloxane-modified cyclodextrin compound of any one of 1 to 5 in an amount of 0.05 to 20% by weight of the cosmetic composition.

7. The cosmetic composition of 6 further comprising water, the composition being in emulsion form.

8. The cosmetic composition of 6 or 7 further comprising at least one ingredient selected from silicone oils, hydrocarbon oils, ester oils, glyceride oils, and UV absorbers.

9. The cosmetic composition of any one of 6 to 8 further comprising a powder, the composition being liquid, paste or solid.

Advantageous Effects of Invention

The invention provides a novel organopolysiloxane-modified cyclodextrin compound. The cyclodextrin compound is able to enhance the blending stability of oils, typically silicone oil, in cosmetics. A cosmetic composition having the cyclodextrin compound blended therein is effectively spreadable and free of greasy or sticky feel, and gives a dry light feel characteristic of silicone oil. Since the cyclodextrin compound is effectively adhesive to the skin, it improves the lasting performance of cosmetics. When a cosmetic composition further contains pharmaceutical, fragrant or other components, the invention provides a cosmetic composition in which these components can be blended in a stable manner.

DESCRIPTION OF EMBODIMENTS

Now the invention is described in detail.

[Component (A)]

The invention provides an organopolysiloxane-modified cyclodextrin compound composed of sugar units having the formula (1):

[Chem. 7]

(1)

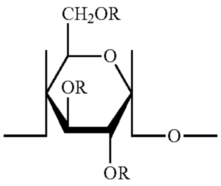

wherein R is independently hydrogen, a group having the formula (2):

[Chem. 8]

(2)

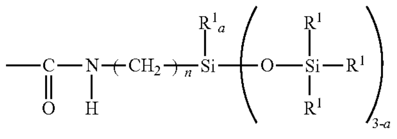

wherein $R^1$ is independently a group selected from among C1-C8 alkyl groups, C1-C8 fluorine-substituted alkyl groups, C6-C12 aryl groups, and C7-C12 aralkyl groups, n is an integer of 1 to 10, and a is an integer of 0 to 3, or a group having the formula (3):

[Chem. 9]

(3)

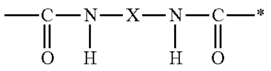

wherein X is a divalent organic group, and * is a point of attachment to a hydroxyl group of another sugar unit, wherein the ratio of the molar number $N_H$ of the hydrogen, the molar number $N_S$ of the group having formula (2), and the molar number $N_L$ of the group having formula (3) per mole of the organopolysiloxane-modified cyclodextrin compound is $N_H$:$N_S$:$N_L$=(0.5 to 2.5):(0.3 to 2.0):(0.1 to 0.5) and $N_H+N_S+N_L=3.0$.

It preferably has a cyclodextrin structure in which the sugar unit having formula (1) is derived from a cyclodextrin compound selected from α-cyclodextrin, β-cyclodextrin, γ-cyclodextrin, and derivatives of the foregoing cyclodextrins having a hydroxyethyl or hydroxypropyl group.

R in formula (1) is independently a group selected from hydrogen, a triorganosilyl-modified amide group having formula (2), and a linking group having a divalent urethane bond, represented by formula (3). R is selected such that the ratio of the molar number $N_H$ of hydrogen, the molar number $N_S$ of the group having formula (2), and the molar number $N_L$ of the group having formula (3) per mole of the organopolysiloxane-modified cyclodextrin compound is $N_H$:$N_S$:$N_L$=(0.5 to 2.5):(0.3 to 2.0):(0.1 to 0.5) and $N_H+N_S+N_L=3.0$.

In the triorganosilyl-modified amide group having formula (2), $R^1$ is independently a group selected from among C1-C8 alkyl groups, C1-C8 fluorine-substituted alkyl groups, C6-C12 aryl groups, and C7-C12 aralkyl groups. Exemplary alkyl groups include straight alkyl groups such as methyl, ethyl, propyl, butyl, pentyl, hexyl, heptyl, and octyl, and cycloalkyl groups such as cyclopentyl and cyclohexyl. Exemplary aryl groups include aryl groups such as phenyl and tolyl. Exemplary aralkyl groups include benzyl and phenethyl. Exemplary fluorine-substituted alkyl groups include trifluoropropyl and heptadecafluorodecyl. Inter alia, CT-C8 alkyl groups and phenyl groups are preferred, with methyl being most preferred.

The subscript n is an integer of 1 to 10, preferably 2 to 6, most preferably 3; and "a" is an integer of 0 to 3, most preferably 3. Within the range, the resulting organopolysiloxane-modified cyclodextrin compound is more improved in compatibility with oils, typically silicone oils. Also, a cosmetic composition comprising such an organopolysiloxane-modified cyclodextrin compound is effectively spreadable and has a non-sticky pleasant feeling on use.

In the linking group having a divalent urethane bond, represented by formula (3), X is a divalent organic group, and * is a point of attachment to a hydroxyl group of another sugar unit. Now that a urethane bond is used to link cyclodextrins together, the compound has self-association due to interaction between molecules and allows an oil, typically silicone oil to exhibit a viscosity buildup. Adjusting the amount of urethane bond ensures that a cosmetic composition having the cyclodextrin compound blended therein eliminates a sticky feel and is so adhesive to the skin that its lasting performance is improved.

The divalent organic group X is a C1-C10 divalent aliphatic hydrocarbon group, C6-C20 divalent aromatic hydrocarbon group, or divalent group having a siloxane bond in the backbone, represented by formula (4). It is preferred that X is a divalent group represented by formula (4), which means that a siloxane bond is included in a site for linking cyclodextrins together, because the compatibility with an oil, typically silicone oil is more improved and the range of oils whose blending stability is improved is expanded.

Examples of the C1-C10 divalent aliphatic hydrocarbon group include C1-C10 alkylene groups and C5-C10 cycloalkylene groups. Specific examples include methylene, ethylene, trimethylene, ethylidene, isopropylidene, tetramethylene, pentamethylene, hexamethylene, cyclohexylene, and divalent hydrocarbon groups having cyclohexyl ring derived from isophorone diisocyanate.

Examples of the C6-C20 divalent aromatic hydrocarbon group include 1,3-phenylene, 1,4-phenylene, 2-methyl-1,3-phenylene, 4-methyl-1,3-phenylene, and diphenylmethane-4,4'-diyl. Of the foregoing divalent hydrocarbon groups, hexamethylene and divalent hydrocarbon groups having cyclohexyl ring derived from isophorone diisocyanate are preferred.

The divalent group having a siloxane bond in the backbone is represented by formula (4):

[Chem. 10]

(4)

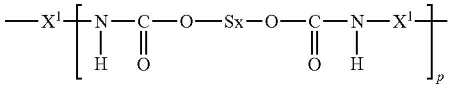

wherein $X^1$ is independently a C1-C10 divalent aliphatic hydrocarbon group or C6-C20 divalent aromatic hydrocarbon group, Sx is a divalent organopolysiloxane residue having the formula (5):

[Chem. 11]

(5)

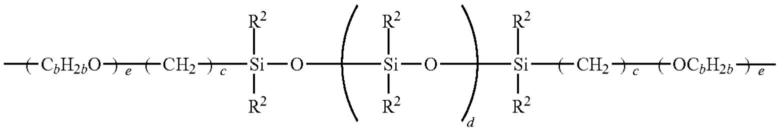

wherein $R^2$ is independently a group selected from among C1-C8 alkyl groups, C1-C8 fluorine-substituted alkyl groups, C6-C12 aryl groups, and C7-C12 aralkyl groups, b is independently a number of 2 to 4, c is independently an integer of 2 to 12, d is independently an integer of 0 to 200, e is independently a number of 0 to 40, and p is a number of 1 to 5.

In the divalent group having a siloxane bond in the backbone, represented by formula (4), $X^1$ is independently a C1-C10 divalent aliphatic hydrocarbon group or C6-C20 divalent aromatic hydrocarbon group. Specific and preferred examples of these groups are as exemplified above for X. In formula (4), p is a number of 1 to 5, preferably 1 to 3. As long as p is not more than 5, the molecular weight of the organopolysiloxane-modified cyclodextrin compound is reduced, and when it is blended in a cosmetic composition, its solubility in oil becomes better and blending stability is more improved.

Sx is a divalent group having a siloxane bond in the backbone, represented by formula (5). In formula (5), $R^2$ is independently a group selected from among C1-C8 alkyl groups, C1-C8 fluorine-substituted alkyl groups, C6-C12 aryl groups, and C7-C12 aralkyl groups. Specific and preferred examples of these groups are as exemplified above for $R^1$. The subscript b is independently a number of 2 to 4, preferably 2 or 3; c is independently an integer of 2 to 12, preferably 2 or 3; d is independently an integer of 0 to 200, preferably 0 to 100, more preferably 1 to 80; e is independently a number of 0 to 40, preferably 0 to 20, more preferably 1 to 15.

The ratio of the molar number $N_H$ of hydrogen, the molar number $N_S$ of the group having formula (2), and the molar number $N_L$ of the group having formula (3) per mole of the organopolysiloxane-modified cyclodextrin compound, that is, the proportion or ratio in which hydrogen of three hydroxyl groups in each of the sugar units of which the organopolysiloxane-modified cyclodextrin compound is composed is substituted by a triorganosilyl-modified amide group having formula (2) and a divalent organic group having formula (3) is as follows.

$$N_H:N_S:N_L=(0.5\text{ to }2.5):(0.3\text{ to }2.0):(0.1\text{ to }0.5)\text{ with the proviso: }N_H+N_S+N_L=3.0.$$

$N_H$: the molar number of hydrogen $N_S$: the molar number of formula (2)

$N_L$: the molar number of formula (3)

The ratio $N_H:N_S:N_L$ is preferably (0.5 to 2.5):(0.4 to 2.0):(0.1 to 0.5), more preferably (1.0 to 2.45):(0.45 to 1.75):(0.1 to 0.4).

As understood from the above-defined ratio, it is unnecessary that all hydroxyl groups are substituted by the substituent group having formula (2) and/or the substituent group having formula (3). It is characteristic that some hydroxyl groups remain in the sugar units. Since the solubility in oil, degree of crosslinking, and molecular weight vary with the ratio, substituent groups may be combined in accordance with a particular oil used. Although the organopolysiloxane-modified cyclodextrin compound can be blended in a cosmetic composition as such, the cyclodextrin compound, which is normally solid, is preferably blended in a cosmetic composition after it is dissolved or gelled in an oil. The oil used herein may be the same as the oil which can be blended in the inventive cosmetic composition.

[Method of Preparing Organopolysiloxane-Modified Cyclodextrin Compound]

Next, the method of preparing the organopolysiloxane-modified cyclodextrin compound is described. The cyclodextrin compound can be prepared by urethane bond-forming reaction of a cyclodextrin having corresponding sugar units or a derivative thereof with an isocyanate-containing organopolysiloxane having the formula (6):

[Chem. 12]

(6)

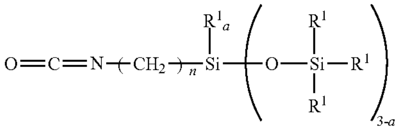

wherein $R^1$, n and a are as defined above and a diisocyanate having the formula (7):

[Chem. 13]

(7)

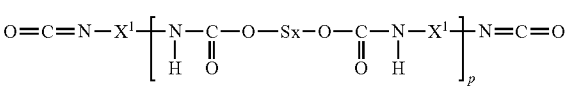

wherein $X^1$ and Sx are as defined above, and p is 0 to 5. Specifically, there may be employed either the method of mixing all three components for reaction or the method of reacting a cyclodextrin or a derivative thereof with one of the isocyanate-containing organopolysiloxane having formula (6) and the diisocyanate compound having formula (7) and then reacting with the other one. The ratio of $N_H:N_S:N_L$ may be adjusted in terms of the type and amount of reactants or the like in this step.

The cyclodextrin or derivative thereof is a cyclodextrin compound selected from α-cyclodextrin, β-cyclodextrin, γ-cyclodextrin, and derivatives of the foregoing cyclodextrins having a hydroxyethyl or hydroxypropyl group. The cyclodextrin or derivative thereof is preferably subjected to the preparation after it is previously heat dried to remove any water included therein.

Also, the diisocyanate having formula (7) may be a prepolymer which is obtained by reacting an α,ω-dihydroxy-modified organopolysiloxane having the formula (8):

[Chem. 14]

(8)

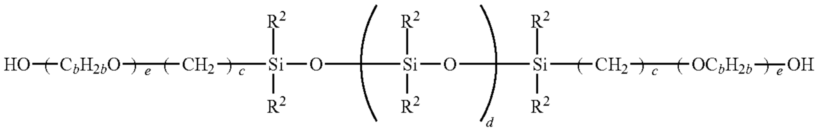

wherein $R^2$, b, c, d, and e are as defined above with a diisocyanate compound having the formula (9):

[Chem. 15]

$$O{=}C{=}N{=}X^1{=}N{=}C{=}O \qquad (9)$$

wherein $X^1$ is as defined above.

Illustrative examples of the isocyanate-containing organopolysiloxane having formula (6) are shown below.

[Chem. 16]

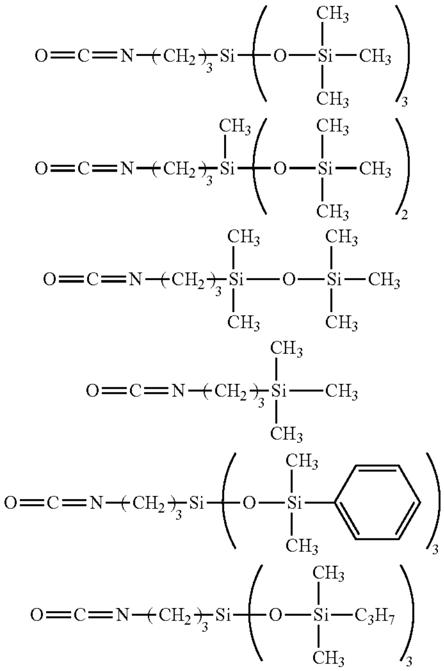

The diisocyanate compound having formula (9) is preferably at least one compound selected from among hexamethylene diisocyanate, 4,4'-diphenylmethane diisocyanate, 1,4'-phenylene diisocyanate, toluene diisocyanate, and isophorone diisocyanate, more preferably hexamethylene diisocyanate or 4,4'-diphenylmethane diisocyanate.

Also, it is preferred from the aspects of reaction efficiency improvement and reaction control to use a solvent in the reaction. Examples of the solvent used herein include esters such as butyl acetate, ketones such as methyl ethyl ketone, methyl isobutyl ketone and cyclohexanone, aromatic hydrocarbons such as toluene and xylene, ethers such as dibutyl ether, tetrahydrofuran, and dioxane, and amides such as N,N-dimethylformamide and N-methylpyrrolidone. They may be used alone or in admixture of two or more.

The reaction is typically performed at 20 to 150° C. for 1 to 10 hours, depending on the use and type of the solvent. The addition of the isocyanate compound may be sequential dropwise addition, dropwise addition of a mixture, or simultaneous addition. There may be added any of well-known catalysts which are used in urethane bond formation, for example, amines such as triethylamine, triethylenediamine and N-methylmorpholine, and organometallic compounds such as di-n-butyltin dilaurate and stannous oleate. On washing and drying at the end of reaction, the target organopolysiloxane-modified cyclodextrin compound is obtainable.

[Gelling Agent]

The organopolysiloxane-modified cyclodextrin compound of the invention is useful as a gelling agent for oils. Examples of the oil include silicone oils, hydrocarbon oils, ester oils, glyceride oils, natural animal or plant oils and fats, and semi-synthetic oils and fats, as well as UV absorbers and mixtures thereof, which may be used alone or in admixture of two or more. Inter alia, the oil to be gelled is preferably selected from silicone oils and hydrocarbon oils, for example, cyclic silicones such as decamethylcyclopentasiloxane and dodecamethylcyclohexasiloxane, linear silicones such as hexamethyldisiloxane, octamethyltrisiloxane, decamethyltetrasiloxane, dodecamethylpentasiloxane, and tetradecamethylhexasiloxane, branched silicones such as tristrimethylsiloxymethylsilane, straight hydrocarbon oils such as decane, undecane and dodecane, and branched hydrocarbon oils such as isododecane. In case of gelation, the amount of the organopolysiloxane-modified cyclodextrin compound blended in the cosmetic composition is 3 to 20% by weight of the cosmetic composition.

[Cosmetic Composition]

The organopolysiloxane-modified cyclodextrin compound of the invention is suited as an ingredient in skin care cosmetics, make-up cosmetics, UV-protective cosmetics, and hair cosmetics. The amount of the cyclodextrin compound blended is preferably 0.05 to 20% by weight, more preferably 0.05 to 10% by weight of the cosmetic composition. With the amount in the range, the cosmetic composition has a dry light feeling characteristic of silicone oil, blending stability and long-lasting performance. Further, any of optional components may be blended alone or in admixture of two or more in an amount not impairing the benefits of the invention. The name of ingredients is sometimes expressed by the Japanese labeling name or the International Nomenclature for Cosmetic Ingredients (INCI). The English description is omitted when the labeling name corresponds to INCI.

Water

The cosmetic composition of the invention further contains water and may take an emulsion form. When water is blended, its amount is preferably 1 to 95% by weight, more preferably 20 to 80% by weight of the cosmetic composition, though it varies with the type of the composition.

Oil

The cosmetic composition may further contain one or more of silicone oils, hydrocarbon oils, ester oils, glyceride oils, natural animal or plant oils and fats, and semi-synthetic oils and fats, as well as UV absorbers, specifically one or more of silicone oils, hydrocarbon oils, ester oils, glyceride oils, and UV absorbers, or mixtures thereof. Any of these oils in gel form is also acceptable.

As the oil, any of solid, semi-solid and liquid oils may be used as long as they are used in conventional cosmetics.

Examples of the silicone oil used herein include cyclotetrasiloxane (INCI), cyclopentasiloxane (INCI), cyclohexasiloxane (INCI), dimethicone (INCI), methyl trimethicone (INCI), tetrakistrimethylsiloxysilane, caprylyl methicone (INCI), phenyl trimethicone (INCI), diphenylsiloxyphenyl trimethicone (INCI), diphenyl dimethicone (INCI), trifluoromethyl alkyl(C1-4) dimethicone, amodimethicone (INCI), aminopropyl dimethicone (INCI), and PCA dimethicone (INCI).

The hydrocarbon oils include straight or branched hydrocarbon oils while they may be volatile. Examples of the hydrocarbon oil include olefin oligomers (INCI), isoparaffin such as C13 or C14 isoparaffin (INCI), isododecane (INCI), undecane (INCI), dodecane (INCI), isohexadecane (INCI), hydrogenated polyisobutene (INCI: Hydrogenated Polyisobutene), squalane (INCI), mineral oil (INCI), and alkanes such as coconut alkane (INCI) and (C13-15) alkane (INCI).

Examples of the ester oil include diisobutyl adipate (INCI: Diisobutyl Adipate), dihexyldecyl adipate (labeling name), diheptylundecyl adipate (INCI: Diheptylundecyl Adipate), n-alkyl glycol monoisostearates such as isostearyl isostearate (INCI: Isostearyl Isostearate), isocetyl isostearate (INCI: Isocetyl Isostearate), trimethylolpropane triisostearate (INCI: Trimethylolpropane Triisostearate), glycol diethylhexanoate (INCI: Glycol Diethylhexanoate), cetyl ethylhexanoate (INCI: Cetyl Ethylhexanoate), trimethylolpropane triethylhexanoate (INCI: Trimethylolpropane Triethylhexanoate), pentaerythrityl tetraethylhexanoate (INCI: Pentaerythrityl Tetraethylhexanoate), cetyl octanoate (INCI: Cetyl Ethylhexanoate), octyldodecyl esters such as octyldodecyl stearoyloxystearate (INCI: Octyldodecyl Stearoyl Stearate), oleyl oleate (INCI: Oleyl Oleate), octyldodecyl oleate (INCI: Octyldodecyl Oleate), decyl oleate (INCI: Decyl Oleate), neopentyl glycol dioctanoate (INCI: Neopentyl Glycol Diethylhexanoate), neopentyl glycol dicaprate (INCI: Neopentyl Glycol Dicaprate), diisostearyl malate (INCI: Diisostearyl Malate), triethyl citrate (INCI: Triethyl Citrate), diethylhexyl succinate (INCI: Diethylhexyl Succinate), amyl acetate (INCI: Amyl Acetate), ethyl acetate (INCI: Ethyl Acetate), butyl acetate (INCI: Butyl Acetate), isocetyl stearate (INCI: Isocetyl Stearate), butyl stearate (INCI: Butyl Stearate), diisopropyl sebacate (INCI: Diisopropyl Sebacate), diethylhexyl sebacate (INCI: Diethylhexyl Sebacate), cetyl lactate (INCI: Cetyl Lactate), myristyl lactate (INCI: Myristyl Lactate), isononyl isononanoate (INCI: Isononyl Isononanoate), isotridecyl isononanoate (INCI: Isotridecyl Isononanoate), palmitates such as isopropyl palmitate (INCI: Isopropyl Palmitate), ethylhexyl palmitate (INCI: Ethylhexyl Isopalmitate), and hexyldecyl palmitate (INCI: Isocetyl Palmitate, Hexyldecyl Palmitate), cholesteryl hydroxystearate (INCI: Cholesteryl Hydroxystearate), myristates such as isopropyl myristate (INCI: Isopropyl Myristate), octyldodecyl myristate (INCI: Octyldodecyl Myristate), and myristyl myristate (INCI: Myristyl Myristate), ethylhexyl laurate (INCI: Ethylhexyl Laurate), hexyl laurate (INCI: Hexyl Laurate), dioctyldodecyl lauroyl glutamate (INCI: Dioctyldodecyl Lauroyl Glutamate), and isopropyl lauroyl sarcosinate (INCI: Isopropyl Lauroyl Sarcosinate).

Examples of the glyceride oil include triethylhexanoin (INCI), glyceryl tri(caprylate/caprate) (INCI: Caprylic/Capric Triglyceride), cocoglyceryl (INCI), triglyceryl (caprylate/caprate/succinate) (INCI: Caprylic/Capric/Succinic Triglyceride), and caprylic/capric glycerides (INCI).

Besides the foregoing, any of the following oils may be used in accordance with a particular purpose. Examples of the natural animal and plant oils and fats and semi-synthetic oils and fats include avocado oil (INCI: *Persea Gratissima* (Avocado) Oil), linseed oil (INCI: *Linum Usitatissimum* (Linseed) Seed Oil), almond oil (INCI: *Prunus Amygdalus Dulcis* (Sweet Almond) Oil), Chinese wax, perilla oil (labeling name), olive oil (INCI: *Olea Europaea* (Olive) Fruit Oil), cocoa butter, kapok wax, California nutmeg oil (INCI: *Torreya Califomica* (Calfomia Nutmeg) Oil), citronella grass oil (INCI: Cymbopogon Nardus (Citronella) Oil), *Torreya Nucifera* seed oil (INCI: *Torreya Nucifera* Seed Oil), camauba wax (INCI: *Copermicia Cerifera* (Camauba) Wax), liver oil, candelilla wax (INCI: *Euphorbia Cerifera* (Candelilla) Wax), purified candelilla wax, tallow, beef foot oil, beef bone oil, hydrogenated tallow, kyounin oil (INCI: Kyounin Yu), whale wax, hydrogenated oil, wheat germ oil (INCI: *Triticum Vulgare* (Wheat) Germ Oil), sesame oil (INCI: *Sesamum Indicum* (Sesame) Seed Oil), rice germ oil (INCI: *Oryza Sative* (Rice) Germ Oil), rice bran oil (INCI: *Oryza Sativa* (Rice) Bran Oil), sugarcane wax (INCI: *Saccharum Officinarum* (Sugarcane) Wax), camellia oil (INCI: *Camellia Kissi* Seed Oil), safflower oil (INCI: *Carthamus Tinctorius* (Safflower) Seed Oil), shea butter (INCI: *Butyrospermum Parkii* (Shea Butter)), palm kernel oil, cinnamon oil, jojoba wax, squalane (INCI), squalene (INCI), shellac wax, turtle oil (INCI: Turtle Oil), soybean oil (INCI: *Glycine Soja* (Soybean) Oil), camellia seed oil (INCI: *Camellia Sinensis* Seed Oil), Japanese camellia oil (INCI: *Camellia Japonica* Seed Oil), primrose oil (INCI: *Oenothera Biennis* (Evening Primrose) Oil), corn germ oil (INCI: *Zea Mays* (Corn) Germ Oil), lard (INCI: Lard), rapeseed oil, Japanese vernicia oil, rice bran wax (INCI: *Oryza Sativa* (Rice) Bran Wax), germ oil, horse fat (INCI: Horse Fat), persic oil (labeling name), palm oil (INCI: *Elaeis Guineensis* (Palm) Oil), palm kernel oil (INCI: *Elaeis Guineensis* (Palm) Kernel Oil), castor oil (INCI: *Ricinus Communis* (Castor) Seed Oil), hydrogenated castor oil, castor oil fatty acid methyl ester, sunflower oil (INCI: *Helianthus Annuus* (Sunflower) Seed Oil), grape seed oil (INCI: *Vitis Vinifera* (Grape) Seed Oil), bayberry wax, jojoba seed oil (INCI: *Simmondsia Chinensis* (Jojoba) Seed Oil), macadamia seed oil (INCI: *Macadamia Temifolia* Seed Oil), macadamia nut oil (INCI: *Macadamia Integrifolia* Seed Oil), beeswax (INCI: Beeswax), mink oil, meadowfoam oil (INCI: *Limnanthes Alba* (Meadowfoam) Seed Oil), cotton seed oil (INCI: *Gossypium Herbaceum* (Cotton) Seed Oil), cotton wax, Japan wax (INCI: *Rhus Succedanea* Fruit Wax), Japan kernel oil, montan wax (INCI: Montan Wax), coconut oil (INCI: *Cocos Nucifera* (Coconut) Oil), hydrogenated coconut oil, ti-coconut oil fatty acid glyceride, sheep fat, peanut oil (INCI: *Arachis Hypogaea* (Peanut) Oil), lanolin (INCI: Lanolin), liquid lanolin (INCI: Lanolin Oil), reduced lanolin, lanolin alcohol (INCI), hard lanolin, lanolin acetate, acetic acid lanolin alcohol (INCI: acetylated Lanolin Alcohol), lanolin fatty acid isopropyl (INCI: Isopropyl Lanolate), POE lanolin alcohol ether, POE lanolin alcohol acetate, lanolin fatty acid polyethylene glycol, POE hydrogenated lanolin alcohol ether, and egg yolk oil (INCI: Egg Oil). Notably, POE designates polyoxyethylene.

Examples of the higher alcohol include lauryl alcohol (INCI), myristyl alcohol (INCI), palmityl alcohol, stearyl alcohol (INCI), behenyl alcohol (INCI), hexadecyl alcohol (INCI), oleyl alcohol (INCI), isostearyl alcohol (INCI), hexyldodecanol, octyldodecanol (INCI), cetostearyl alcohol, 2-decyltetradecinol, cholesterol (INCI), phytosterol (INCI), POE cholesterol ether, monostearyl glycerin ether (batyl alcohol), and monooleyl glyceryl ether (selachyl alcohol).

When used, the amount of the oil blended is preferably 1 to 98% by weight of the cosmetic composition although the amount varies with the type of the composition.

The UV absorber used herein may be any of solid, semisolid and liquid UV absorbers as long as they are used in conventional cosmetics.

Examples include homosalate (INCI), octocrylene (INCI), t-butyl methoxydibenzoylmethane (INCI: Butyl Methoxydibenzoylmethane), ethylhexyl salicylate (INCI: Ethylhexyl Salicylate), diethylaminohydroxybenzoyl hexyl benzoate (INCI: Diethylamino Hydroxybenzoyl Hexyl Benzoate), oxybenzone-6 (INCI: Benzophenone-6), oxybenzone-9 (INCI: Benzophenone-9), oxybenzone-1 (INCI: Benzophenone-1), polysilicone-15 (INCI), dimethoxybenzylidene dioxoimidazolidine octyl propionate (INCI: Ethylhexyl Dimethoxybenzylidene Dioxoimidazolidine Propionate), oxybenzone-2 (INCI: Benzophenone-2), terephthalylidene dicamphor sulfonic acid (INCI: Terephthalylidene Dicamphor Sulfonic Acid), ethylhexyl triazone (INCI), methylbis(trimethylsiloxy)silyl isopentyl trimethoxycinnamate (INCI: Isopentyl Trimethoxycinnamate Trisiloxane), drometrizole trisiloxane (INCI), dimethyl PABA ethylhexyl (INCI: Ethylhexyl Dimethyl PABA), isopropyl para-methoxycinnamate (INCI: Isopropyl Methoxycinnamate), ethylhexyl methoxycinnamate (INCI: Ethylhexyl Methoxycinnamate), bisethylhexyloxyphenol methoxyphenyltriazine (INCI: Bis-Ethylhexyloxyphenol Methoxyphenyl Triazine), oxybenzone-3 (INCI: Benzophenone-3), oxybenzone-4 (INCI: Benzophenone-4), oxybenzone-5 (INCI: Benzophenone-5), phenylbenzimidazole sulfonic acid (INCI: Phenylbenzimidazole Sulfonic Acid), methylene bisbenzotriazolyl tetramethylbutylphenol (INCI: Methylene Bis-Benzotriazolyl Tetramethylbutylphenol), glyceryl ethylhexanoate dimethoxycinnamate (INCI: Glyceryl Ethylhexanoate Dimethoxycinnamate), glyceryl PABA (INCI: Glyceryl PABA), methyl diisopropylcinnamate (INCI: Diisopropyl Methyl Cinnamate), cinoxate (INCI), ethylhexyl dimethoxybenzylidene dioxoimidazolidine propionate (INCI: Ethylhexyl Dimethoxybenzylidene Dioxoimidazolidine Propionate), etc.

UVA absorbers, e.g., diethylaminohydroxybenzoyl hexyl benzoate (INCI: Diethylamino Hydroxybenzoyl Hexyl Benzoate) and UVB absorbers, e.g., ethylhexyl methoxcinnamate (INCI: Ethylhexyl Methoxycinnamate) may be used in combination. Also, each of them may be used in admixture. When used, the amount of the UV absorber blended is preferably 0.1 to 30% by weight of the cosmetic composition although the amount varies with the type of the composition.

Powder

The cosmetic composition of the invention may further contain a powder. The composition may take any of liquid, paste and solid forms in which the powder is dispersed. The cosmetic composition containing the powder experiences no changes like agglomeration of the powder and has improved powder dispersion stability. As long as the composition takes any of liquid, paste and solid forms, it is convenient to handle and applicable to a variety of cosmetics.

The powder used herein may be any of powders which are used in conventional cosmetics without limits with respect to shape (spherical, needle and plate), particle size (fumed, microparticulate and pigment grade), and particle structure (porous and nonporous) while one or more of powders may be used. Exemplary powders include inorganic powders, organic powders, surfactant metal salt powders, colored pigments, pearl pigments, metal powder pigments, tar dyes, and natural dyes.

Specifically, examples of the inorganic powder include titanium oxide (INCI: Titanium Dioxide), zirconium oxide (INCI: Zirconium Dioxide), zinc oxide (INCI Zinc Oxide), cerium oxide (INCI: Cerium Oxide), magnesium oxide (INCI: Magnesium Oxide), barium sulfate, calcium sulfate, magnesium sulfate, calcium carbonate, magnesium carbonate, talc (INCI: Talc), mica (INCI: Mica), kaolin (INCI: Kaolin), sericite, titanate mica, silica (INCI: Silica), hydrated silica (INCI: Hydrated Silica), aluminum silicate (INCI: Aluminum Silicate), magnesium silicate (INCI: Magnesium Silicate), magnesium aluminum silicate (INCI: Magnesium Aluminum Silicate), calcium silicate (INCI: Calcium Silicate), hydroxyapatite (INCI: Hydroxyapatite), bentonite (INCI: Bentonite), montmorillonite (INCI: Montmorillonite), hectorite (INCI: Hectorite), zeolite (INCI: Zeolite), alumina (INCI: Alumina), aluminum hydroxide (INCI: Aluminum Hydroxide), and boron nitride (INCI: Boron Nitride).

Examples of the organic powder include polyamide, polyester, polyethylene (INCI: Polyethylene), polypropylene (INCI: Polypropylene), polystyrene (INCI: Polystyrene), polyurethane (INCI: Polyurethane), polymethyl methacrylate (INCI: Polymethyl methacrylate), cellulose (INCI: Cellulose), silk, nylon, and silicones (INCI: Vinyl Dimethicone/Methicone Crosspolymer, Polymethylsilsesquioxane, Vinyl Dimethicone/Methicone Silsesquioxane Crosspolymer, Diphenyl Dimethicone/Vinyl Diphenyl Dimethicone/Silsesquioxane Crosspolymer, Polysilicone-1 Crosspolymer, and Polysilicone-22).

Examples of the surfactant metal salt powder (or metal soap) include zinc stearate (INCI: Zinc Stearate), aluminum stearate, calcium stearate, magnesium stearate, zinc myristate (INCI: Zinc Myristate), and magnesium myristate.

Examples of the colored pigment include inorganic red pigments such as iron oxide (INCI: Iron Oxide), iron hydroxide and iron titanate, inorganic brown pigments such as γ-iron oxide, inorganic yellow pigments such as yellow iron oxide (Yellow Oxide of Iron) and loess (INCI: Yellow Ocher), inorganic black pigments such as black iron oxide (Black Oxide of Iron) and carbon black (INCI: Carbon Black), inorganic purple pigments such as manganese violet (INCI: Manganese Violet), inorganic green pigments such as chromium hydroxide (INCI: Chromium Hydroxide Green), chromium oxide (INCI: Chromium Oxide Green), and cobalt titanate (INCI: Cobalt Titanium Oxide), inorganic blue pigments such as Prussian blue (Iron Blue) and ultramarine, and synthetic resin powders in composite form of these powders.

Examples of the pearl pigment include titanium oxide-coated mica, titanium oxide-coated mica, bismuth oxychloride, titanium oxide-coated bismuth oxychloride, titanium oxide-coated talc, fish scale flakes, and titanium oxide-coated colored mica.

Examples of the metal powder pigment include aluminum powder and copper powder (INCI: Copper Powder).

Suitable tar dyes include Red #3 (Erythrosine), Red #104 (Phloxine B), Red #106 (Acid red), Red #201 (Lithol rubine B), Red #202 (Lithol rubine BCA), Red #204 (Lake red CBA), Red #205 (Lithol red), Red #220 (Deep maroon), Red #226 (Helindone pink CN), Red #227 (Fast acid magenta), Red #228 (Parmatone red), Red #230 (Eosine YS), Red #401 (Violamine R), Red #505 (Oil red XO), Yellow #4 (Tartrazin), Yellow #5 (Sunset yellow FCF), Yellow #202 (Uranine K), Yellow #203 (Quinolin yellow WS), Yellow #204 (Quinolin yellow SS), Yellow #401 (Hanza yellow), Blue #1 (Brilliant blue FCF), Blue #2 (Indigo carmine), Blue #201 (Indigo), Blue No. 404 (Phtalocyanine blue), Green #3 (Fast green FCF), Green #201 (Alizanine cyanine green F), Green #204 (Pyranine conc), Green #205 (Light green SF yellowish), Orange #201 (Dibromofluorescein), Orange #203 (Permanent orange), Orange #204 (Benzidine orange G), Orange #206 (Diiodofluorescein), Orange #207 (Erythrosine yellowish NA).

Exemplary natural dyes include cochineal, laccaic acid (INCI: Laccaic Acid), carthamin, brazilin, and crocin.

These powders may also be used in composite forms of the powders and after treatment with common oils, silicone oils, fluorine compounds, surfactants or the like. Also, powders treated with an alkyl group having a hydrolyzable silyl group or silicon-bonded hydrogen, a straight and/or branched organopolysiloxane having a hydrolyzable silyl group or silicon-bonded hydrogen, a straight and/or branched organopolysiloxane having a hydrolyzable silyl group or silicon-bonded hydrogen and co-modified with a long-chain alkyl, a straight and/or branched organopolysiloxane having a hydrolyzable silyl group or silicon-bonded hydrogen and co-modified with polyoxyalkylene, or an acrylic-silicone copolymer having a hydrolyzable silyl group or silicon-bonded hydrogen may be used if necessary.

Compound Having Alcoholic Hydroxyl Group in Molecular Structure

In the cosmetic composition of the invention, a compound having an alcoholic hydroxyl group in its molecular structure may be used alone or in admixture. Examples of the compound having an alcoholic hydroxyl group which can be added herein include lower alcohols such as ethanol (INCI: Alcohol) and isopropanol (INCI: Isopropyl Alcohol), and sugar alcohols such as sorbitol (INCI) and maltose (INCI) as well as sterols such as cholesterol (INCI), sitosterol (INCI: Beta-Sitosterol), phytosterol (INCI), and lanosterol (INCI), and polyhydric alcohols such as butylene glycol (INCI), propylene glycol (INCI), dibutylene glycol, and pentylene glycol (INCI). When used, the amount of the compound having an alcoholic hydroxyl group in its molecular structure blended is preferably 0.1 to 98% by weight of the cosmetic composition.

Water-Soluble or Water-Swellable Polymer

In the cosmetic composition, a water-soluble or water-swellable polymer may be blended alone or in admixture depending on its purpose. Exemplary polymers include plant base high-molecular weight compounds such as gum arabic (INCI: Acacia Senegal Gum), tragacanth gum (INCI: *Astragalus Gummifer* Gum), galactan, ceratonia silica gum, guar gum (INCI: *Cyamopsis Tetragonoloba* (Guar) Gum), karaya gum (INCI: *Sterculia Urens* Gum), carrageenan (INCI: *Chondrus Crispus* (Carrageenan)), pectin (INCI), agar (INCI: Agar), quince seed gum or *Cydonia oblonga* mill (INCI: *Pyrus Cydonia* Seed), rice starch (INCI: *Oryza Sative* (Rice) Starch), wheat starch (INCI: *Triticum Vulgare* (Wheat) Starch), potato starch (INCI: *Solanum Tuberosum* (Potato) Starch), corn starch, algae colloid, tragacanth gum (INCI: *Astragalus Gummifer* Gum), and locust bean gum; bacterial high-molecular weight compounds such as xanthane gum (INCI), dextran (INCI), succinoglycan (INCI) and pullulan (INCI); animal high-molecular weight compounds such as collagen (INCI), casein (INCI), albumin (INCI) and gelatin (INCI); starch-base high-molecular weight compounds such as sodium carboxymethyl starch (INCI: Sodium Carboxymethyl Starch) and hydroxypropyl starch (INCI: Hydroxypropyl Starch), cellulose-base high-molecular weight compounds such as methyl cellulose (INCI), ethyl cellulose (INCI), methyl hydroxypropyl cellulose (INCI), carboxymethyl cellulose, hydroxymethyl cellulose, hydroxypropyl cellulose (INCI), nitrocellulose (INCI), sodium cellulose sulfate (INCI: Sodium Cellulose Sulfate), sodium carboxymethyl cellulose, microcrystalline cellulose (INCI: Microcrystalline Cellulose), and cellulose powder; alginic acid-base high-molecular weight compounds such as sodium alginate (INCI: Algin) and propylene glycol alginate (INCI: Propylene Glycol Alginate), vinyl-base high-molecular weight compounds such as polyvinyl methyl ether and carboxyvinyl polymer; polyoxyethylene-base high-molecular-weight compounds, polyoxyethylene-base high-molecular-weight compounds, polyoxyethylene polyoxypropylene copolymers, acrylic high-molecular-weight compounds such as sodium polyacrylate (INCI: Sodium Polyacrylate), polyethyl acrylate (INCI: Polyethyl acrylate), polyacrylamide (INCI), and acryloyldimethyl taurine salt copolymer, polyethylene imine, synthetic water-soluble polymers such as cation polymers, and inorganic water-soluble high-molecular-weight compounds such as bentonite (INCI), magnesium aluminum silicate (INCI: Magnesium Aluminum Silicate), montmorillonite (INCI), beidellite, nontronite, saponite, hectorite (INCI) and anhydrous silicic acid. Also included are film-forming agents such as polyvinyl alcohol (INCI) and polyvinyl pyrrolidone (INCI). When used, the amount of the water-soluble or water-swellable high-molecular-weight compound blended is preferably 0.1 to 25% by weight of the cosmetic composition.

In the cosmetic composition, one or more surfactants may be blended depending on its purpose. The surfactant may be anionic, cationic, nonionic, or ampholytic. The surfactant is not particularly limited. Any of such surfactants may be used as long as they are used in conventional cosmetics.

Examples of the anionic surfactant include fatty acid soaps such as sodium stearate and triethanolamine palmitate, alkyl ether carboxylic acids and salts thereof, condensate salts of amino acids and fatty acids, alkane sulfonic acid salts, alkene sulfonic acid salts, sulfonic acid salts of fatty acid esters, sulfonic acid salts of fatty acid amides, sulfonic acid salts of formalin condensates, alkyl sulfate salts, secondary higher alcohol sulfate salts, alkyl and allyl ether sulfate salts, sulfate salts of fatty acid esters, sulfate salts of fatty acid alkylolamides, sulfate salts of Turkey red oil or the like, alkyl phosphoric acid salts, ether phosphoric acid salts, alkyl allyl ether phosphoric acid salts, amide phosphoric acid salts, N-acyl lactic acid salts, N-acyl sarcosine salts, and N-acylamino acid base surfactants. Cationic surfactants include amine salts such as alkyl amine salts, polyamine and aminoalcohol fatty acid derivatives, alkyl quaternary ammonium salts, aromatic quaternary ammonium salts, pyridinium salts, and imidazolium salts.

Examples of the nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, methyl glucoside fatty acid esters, alkyl polyglucosides, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, linear or branched polyoxyalkylene-modified organopolysiloxanes, linear or branched polyoxyalkylene/alkyl-co-modified organopolysiloxanes, linear or branched polyglycerin-modified organopolysiloxane, linear or branched polyglycerin/alkyl-co-modified organopolysiloxane, alkanol amides, sucrose ethers, and sucrose amides. Ampholytic surfactants include betaine, phosphatidylcholine, aminocarboxylic acid salts, imidazoline derivatives, and amidoamine compounds.

Of these, linear or branched organopolysiloxanes having a polyoxyalkylene or polyglycerin chain in the molecule and linear or branched organopolysiloxanes having a polyoxyalkylene or polyglycerin chain and a $C_6$-$C_{20}$ long-chain alkyl group in the molecule are preferred. In these surfactants, the content of the hydrophilic polyoxyalkylene group or polyglycerin residue is preferably 10 to 70% by weight of the molecule. When used, the amount of the surfactant blended is preferably 0.1 to 20% by weight, more preferably 0.2 to 10% by weight of the cosmetic composition.

In the cosmetic composition, one or more silicone resins may be blended depending on its purpose. The silicone resin used herein is preferably an acrylic silicone resin in the form of an acrylic/silicone graft or block copolymer. Also useful is an acrylic silicone resin containing in its molecule at least one moiety selected from pyrrolidone moiety, long-chain alkyl moiety, polyoxyalkylene moiety, fluoroalkyl moiety, and anion moiety such as carboxylic acid.

Further, the silicone resin is preferably a silicone network compound selected from resins composed of $R^{1s}{}_3SiO_{1/2}$ units and $SiO_{4/2}$ units, resins composed of $R^{1s}{}_3SiO_{1/2}$ units, $R^{1s}{}_2SiO_{2/2}$ units and $SiO_{4/2}$ units, resins composed of $R^{1s}{}_3SiO_{1/2}$ units and $R^{1s}SiO_{3/2}$ units, resins composed of $R^{1s}{}_3SiO_{1/2}$ units, $R^{1s}{}_2SiO_{2/2}$ units and $R^{1s}SiO_{3/2}$ units, and resins composed of $R^{1s}{}_3SiO_{1/2}$ units, $R^{1s}{}_2SiO_{2/2}$ units, $R^{1s}SiO_{3/2}$ units, and $SiO_{4/2}$ units wherein $R^{1s}$ is an organic group. Also useful is a silicone network compound containing in its molecule at least one moiety selected from pyrrolidone moiety, long-chain alkyl moiety, polyoxyalkylene moiety, fluoroalkyl moiety, and amino moiety. When used, the amount of the silicone resin blended is preferably 0.1 to 20% by weight, more preferably 1 to 10% by weight of the cosmetic composition.

In the cosmetic composition, a composition consisting of at least one crosslinked organopolysiloxane and an oil which is liquid at room temperature may be blended depending on its purpose. Preferably, the crosslinked organopolysiloxane swells with the liquid oil as a result of being impregnated with an amount of more than its own weight of the liquid oil. Suitable liquid oils used herein include liquid silicones, hydrocarbon oils, ester oils, natural animal and plant oils, semi-synthetic oils and fluorochemical oils as mentioned above. Illustrative examples include low viscosity silicone oils having a kinematic viscosity of 0.65 to 100.0 $mm^2/s$ at 25° C. as measured by an Ostwald viscometer according to JIS Z 8803:2011, liquid paraffin, squalane, hydrocarbon oils such as isododecane and isohexadecane, glyceride oils such as trioctanoin, ester oils such as isotridecyl isononanoate, N-acylglutamates, and lauroylsarcosinates, and natural animal and plant oils such as macadamia nut oil. Preferably, the crosslinked organopolysiloxane crosslinker has at least two vinyl reactive sites in the molecule, and forms a crosslinked structure by reacting with silicon-bonded hydrogen. Examples of the compound having at least two vinyl reactive sites in the molecule include organopolysiloxanes having at least two vinyl groups in the molecule, polyoxyalkylenes having at least two allyl groups in the molecule, polyglycerins having at least two allyl groups in the molecule, and α,ω-alkenyldienes.

Also useful is a crosslinked organopolysiloxane containing in the crosslinked molecule at least one moiety selected from the group consisting of polyoxyalkylene moiety, polyglycerin moiety, long-chain alkyl moiety, alkenyl moiety, aryl moiety, and fluoroalkyl moiety. When used, the amount of the composition consisting of a crosslinked organopolysiloxane and an oil which is liquid at room temperature blended is preferably 0.1 to 80% by weight, more preferably 1 to 50% by weight of the cosmetic composition.

In the cosmetic composition, at least one silicone wax may be blended depending on its purpose. The silicone wax is a silicone-modified olefin wax obtained from addition reaction of an unsaturated group-bearing olefin wax consisting of α-olefin and diene with an organohydrogenpolysiloxane having at least one hydrosilyl group per molecule. As the α-olefin of the olefin wax, α-olefins of 2 to 12 carbon atoms such as ethylene, propylene, 1-butene, 1-hexene, and 4-methyl-1-pentene are preferred. As the diene, butadiene, isoprene, 1,4-hexadiene, vinyl norbornene, ethylidene norbornene, and dicyclopentadiene are preferred. As the organohydrogenpolysiloxane having a hydrosilyl group, those of a linear or siloxane branched structure may be used.

In the cosmetic composition, any of components which are used in conventional cosmetics may be added, for example, oil-soluble gelling agents, resins, antiperspirants, humectants, antibacterial preservatives, antibacterial agents, fragrances, salts, antioxidants, acidity regulators, chelating agents, refreshing agents, anti-inflammatory agents, skin modifying ingredients (e.g., brightening or whitening agents, cell activators, anti-skin-roughening agents, blood flow enhancing agents, skin astringents, antiseborrheic agents), vitamins, amino acids, nucleic acids, hormones, and hair setting agents.

Exemplary oil-soluble gelling agents include metal soaps such as aluminum stearate, magnesium stearate (INCI: Magnesium Stearate), zinc myristate (INCI: Zinc Myristate); amino acid derivatives such as N-lauroyl-L-glutamic acid (INCI: Lauroyl Glutamic Acid) and α,γ-di-n-butylamine; dextrin fatty acid esters such as dextrin palmitate (INCI: Dextrin Palmitate), dextrin stearate (INCI: Dextrin Stearate), and dextrin 2-ethylhexanoate palmitate (INCI: Dextrin Palmitate/Ethylhexanoate); sucrose fatty acid esters such as sucrose palmitate (INCI: Sucrose Palmitate) and sucrose stearate (INCI: Sucrose Stearate); fructooligosaccharide fatty acid esters such as fructooligosaccharide stearate and fructooligosaccharide 2-ethylhexanoate; benzylidene derivatives of sorbitol such as monobenzylidene sorbitol and dibenzylidene sorbitol; and organo-modified clay minerals such as dimethylbenzyldodecylammonium montmorillonite clay and dimethyldioctadecylammonium montmorillonite clay. The cosmetic composition exerts a satisfactory effect even when such oil-soluble gelling agents are not blended.

Examples of the antiperspirant include aluminum chlorohydrate (INCI: Aluminum Chlorohydrate), aluminum chloride (INCI: Aluminum Chloride), aluminum sesquichlorohydrate, zirconyl hydroxychloride, aluminum zirconium hydroxychloride, and aluminum zirconium glycine complex.

Examples of the humectant include glycerin, sorbitol, propylene glycol, dipropylene glycol, 1,3-butylene glycol, pentylene glycol, glucose, xylitol, maltitol, polyethylene glycol, hyaluronic acid, chondroitin sulfate, pyrrolidone carboxylate, polyoxyethylene methyl glucoside, polyoxypropylene methyl glucoside, yolk lecithin, soybean lecithin, phosphatidylcholine, phosphatidylethanolamine, phosphatidylserine, phosphatidylglycerol, phosphatidylinositol, and sphingolipid.

Examples of the antibacterial preservative include alkyl p-hydroxybenzoates, benzoic acid (INCI: Benzoic Acid), sodium benzoate (INCI: Sodium Benzoate), sorbic acid (INCI: Sorbic Acid), potassium sorbate (INCI: Potassium Sorbate), and phenoxyethanol (INCI). Suitable antibacterial agents include benzoic acid, salicylic acid, phenol (INCI), sorbic acid, alkyl p-hydroxybenzoates, p-chloro-m-cresol (INCI), hexachlorophene (INCI), benzalkonium chloride (INCI), chlorhexidine chloride (INCI: chlorhexidine dihydrochloride), trichlorocarbanilide, photosensitizers, and phenoxyethanol.

Fragrances include natural fragrances and synthetic fragrances. Suitable natural fragrances include plant fragrances separated from flowers, leaves, stems, and pericarps, and animal fragrances such as musk and civet. Suitable synthetic fragrances include hydrocarbons such as monoterpene; alcohols such as aliphatic alcohols and aromatic alcohols; aldehydes such as terpene aldehydes and aromatic aldehydes; ketones such as alicyclic ketones; esters such as terpene esters; lactones; phenols; oxides; nitrogen-containing compounds; and acetals.

Salts include inorganic salts, organic acid salts, amine salts, and amino acid salts. Exemplary inorganic salts include sodium, potassium, magnesium, calcium, aluminum, zirconium and zinc salts of inorganic acids such as hydrochloric acid, sulfuric acid, carbonic acid and nitric acid. Exemplary organic acid salts include salts of organic acids such as acetic acid (INCI: Acetic Acid), dehydroacetic acid (INCI: Dehydroacetic Acid), citric acid (INCI: Citric Acid), malic acid (INCI: Malic Acid), succinic acid (INCI: Succinic Acid), ascorbic acid (INCI: Ascorbic Acid), and stearic acid (INCI: Stearic Acid). Exemplary amine salts and amino acid salts include salts of amines such as triethanol amine (INCI: Triethanolamine), and salts of amino acids such as glutamic acid. Also useful are hyaluronic acid (INCI: Hyaluronic Acid), salts such as chondroitin sulfate, aluminum zirconium glycine complex, and neutralized acid-alkali salts used in cosmetic formulation.

Examples of the antioxidant include tocopherol (INCI), p-t-butylphenol, butyl hydroxyanisole (INCI), dibutyl hydroxytoluene (INCI), and phytic acid. Suitable acidity regulators include lactic acid (INCI: Lactic Acid), citric acid (INCI: Citric Acid), glycolic acid (INCI: Glycolic Acid), succinic acid (INCI: Succinic Acid), tartaric acid (INCI: Tartaric Acid), dl-malic acid (INCI: Malic Acid), potassium carbonate (INCI: Potassium Carbonate), sodium hydrogencarbonate (INCI: Sodium Bicarbonate), and ammonium hydrogencarbonate (INCI: Ammonium Bicarbonate). Suitable chelating agents include alanine (INCI), sodium EDTA, sodium polyphosphate (INCI: Sodium Polyphosphate), sodium metaphosphate (INCI: Sodium Metaphosphate), and phosphoric acid. Suitable refreshing agents include L-menthol and camphor. Suitable anti-inflammatory agents include allantoin (INCI), glycyrrhizinic acid (INCI: Glycyrrhizinic Acid) and salts thereof, glycyrrhetinic acid (INCI: Glycyrrhetinic Acid), stearyl glycyrrhetinate (INCI: Stearyl Glycyrrhetinate), tranexamic acid, and azulene (INCI).

Suitable skin modifying ingredients include brightening or whitening agents such as placenta extract, arbutin (INCI), glutathione (INCI), and *Saxifraga Sarmentosa* extract (INCI: *Saxifraga Sarmentosa* extract), cell activators such as royal jelly (INCI), photosensitizers, cholesterol derivatives, and bovine blood extracts; anti-skin-roughening agents; blood flow enhancing agents such as vanillylamide nonanoate, benzyl nicotinate (INCI: Benzyl Nicotinate), β-butoxyethyl nicotinate, capsaicin (INCI), zingerone, cantharides tincture, ichthammol (INCI), caffeine (INCI), tannic acid (INCI: Tannic Acid), α-borneol (INCI), tocopherol nicotinate (INCI: Tocopherol Nicotinate), inositol hexanicotinate, cyclandelate, cinnarizine, tolazoline, acetylcholine, verapamil, cepharanthine, and γ-oryzanol (INCI); skin astringents such as zinc oxide and tannic acid; and antiseborrheic agents such as sulfur and thianthol.

Suitable vitamins include vitamin A family such as vitamin A oil, retinol (INCI), retinol acetate (INCI: Retinyl Acetate), retinol palmitate (INCI: Retinyl Palmitate); vitamin B family, specifically vitamin B2 family such as riboflavin (INCI), riboflavin butyrate (INCI: Riboflavin Tetrabutyrate), and flavin adenine nucleotide (INCI: Disodium Flavine Adenine Dinucleotide), vitamin B6 family such as pyridoxine hydrochloride, pyridoxine dioctanoate, pyridoxine tripalmitate (INCI: Pyridoxine Tripalmitate); vitamin B12 and derivatives thereof, vitamin B15 and derivatives thereof; vitamin C family such as L-ascorbic acid (INCI: Ascorbic Acid), L-ascorbic acid dipalmitic acid ester, L-ascorbic acid-2-sodium sulfate (INCI: Disodium Ascorbyl Sulfate), and dipotassium L-ascorbic acid phosphoric acid diester; vitamin D family such as ergocalciferol (INCI) and cholecalciferol (INCI); vitamin E family such as α-tocopherol (INCI), β-tocopherol (INCI), γ-tocopherol (INCI), dl-α-tocopherol acetate (INCI: Tocopheryl acetate), dl-α-tocopherol nicotinate (INCI: Tocopheryl Nicotinate), and dl-α-tocopherol succinate (INCI: Tocopheryl Succinate); nicotinic acids such as nicotinic acid, benzyl nicotinate, and nicotinic amide; vitamin H, vitamin P, pantothenic acids such as calcium pantothenate, D-pantothenyl alcohol, pantothenyl ethyl ether, acetylpantothenyl ethyl ether; and biotin.

Suitable amino acids include glycine (INCI), valine (INCI), leucine (INCI), isoleucine (INCI), serine (INCI), threonine (INCI), phenylalanine (INCI), arginine (INCI), lysine (INCI), aspartic acid (INCI: Aspartic Acid), glutamic acid (INCI: Glutamic Acid), cystine (INCI), cysteine (INCI), methionine (INCI), and tryptophan (INCI). Typical of the nucleic acid is deoxyribonucleic acid. Suitable hormones include estradiol (INCI) and ethenyl estradiol (INCI).

Examples of the hair setting polymer include ampholytic, anionic, cationic and nonionic high-molecular-weight compounds, e.g., polyvinyl pyrrolidone base polymers such as polyvinyl pyrrolidone (INCI) and vinyl pyrrolidone/vinyl acetate copolymers (INCI); acidic vinyl ether base polymers such as methyl vinyl ether/maleic anhydride alkyl half-ester copolymers, acidic polyvinyl acetate polymers such as vinyl acetate/crotonic acid copolymers, acidic acrylic polymers such as (meth)acrylic acid/alkyl (meth)acrylate copolymers, (meth)acrylic acid/alkyl (meth)acrylate/alkyl acrylic amide copolymers; and ampholytic acrylic polymers such as N-methacryloyl ethyl-N,N-dimethylammonium-α-N-methylcarboxybetaine/alkyl (meth)acrylate copolymers, and hydroxypropyl (meth)acrylate/butyl aminoethyl methacrylate/acrylic acid octylamide copolymers. Also useful are naturally occurring high-molecular-weight compounds such as cellulose or derivatives thereof, keratin and collagen or derivatives thereof.

Examples of the form that the inventive cosmetic composition takes include powder, oily, water-in-oil emulsion, oil-in-water emulsion, nonaqueous emulsion, and multiphase emulsions such as W/O/W and O/W/O.

Exemplary types of the cosmetic composition include skin care cosmetics such as liquid, massage agents, beauty liquids, beauty oils, cleansing agents, deodorants, hand cream, lip cream, and wrinkle-hiding agents; make-up cosmetics such as make-up base, concealer, powder, powder foundation, liquid foundation, cream foundation, oily foundation, cheek color, eye shadow, mascara, eye liner, eye brow, and lipstick; hair care products such as shampoo, rinse, treatment, and setting agents, antiperspirants, UV-protecting cosmetic products such as sunscreen oil, sunscreen emulsion, and sunscreen cream.

In particular, the cosmetic composition containing water and hence, taking emulsion form is suited as make-up base, liquid foundation, sunscreen emulsion, and sunscreen cream.

The inventive cosmetic composition may take a variety of formulas including liquid, emulsion, cream, solid, paste, gel, powder, press, multilayer, moose, spray, stick, and pencil. When the cosmetic composition contains a powder, the composition preferably takes either one of liquid, paste and solid forms having the powder dispersed therein because they are easy to handle.

EXAMPLES

Synthesis Examples, Comparative Synthesis Examples, Examples and Comparative Examples are shown below by way of illustration and not by way of limitation. In Examples, compositional percent (%) is by weight unless otherwise stated. It is noted that exemplary organopolysiloxane-modified cyclodextrin compounds are described in Synthesis Examples and Comparative Synthesis Examples, and exemplary cosmetic composition are described in Examples and Comparative Examples.

Synthesis Example 1

After 10 g of γ-cyclodextrin which had been dried at 110° C. for 2 hours and 120 g of N-methylpyrrolidone were dissolved by heating at 80° C., 0.5 g of triethylamine and 2.5 g of hexamethylene diisocyanate were added. The solution was stirred at 100° C. for 3 hours for reaction. Thereafter, 29.2 g of isocyanate-containing organopolysiloxane having the general formula (10) was added dropwise.

[Chem. 17]

(10)

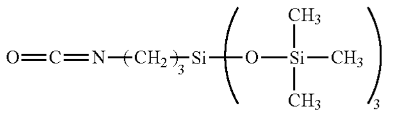

The solution was stirred at 110° C. for 3 hours for reaction. With stirring, the reaction solution was added to 500 g of water. The resulting precipitate was collected by filtration, washed twice with 300 g of water, and further twice with 300 g of a 1/1 (weight ratio) water/methanol mixture. On drying, 33.9 g of white solid was obtained (yield 81.3%). It was analyzed for substitution molar ratio of hydroxyl group by $^1$H-NMR spectroscopy. There was obtained an organopolysiloxane-modified cyclodextrin compound in which for R in the sugar unit having the following formula (11), the ratio of hydrogen:monovalent group having the following formula (11-1): divalent group having the following formula (11-2) is 1.61:1.15:0.24.

[Chem. 18]

(11)

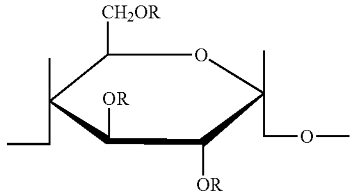

(11-1)

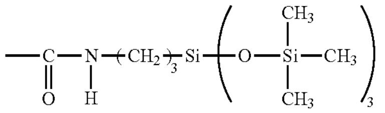

(11-2)

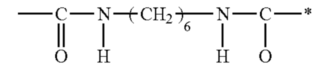

Herein, * designates a point of attachment to a hydroxyl group in another sugar unit.

Synthesis Example 2

After 10 g of 3-cyclodextrin which had been dried at 110° C. for 2 hours and 120 g of N-methylpyrrolidone were dissolved by heating at 80° C., 0.5 g of triethylamine and 6.17 g of 4,4'-diphenylmethane diisocyanate were added. The solution was stirred at 100° C. for 3 hours for reaction. Thereafter, 40.9 g of isocyanate-containing organopolysiloxane having formula (10) was added dropwise.

The solution was stirred at 110° C. for 3 hours for reaction. With stirring, the reaction solution was added to 500 g of water. The resulting precipitate was collected by filtration, washed twice with 300 g of water, and further twice with 300 g of a 1/1 (weight ratio) water/methanol mixture. On drying, 46.8 g of white solid was obtained (yield 82.0%). It was analyzed for substitution molar ratio of hydroxyl group by $^1$H-NMR spectroscopy. There was obtained an organopolysiloxane-modified cyclodextrin compound in which for R in the sugar unit having formula (11), the ratio of hydrogen:monovalent group having formula (11-1): divalent group having the following formula (11-3) is 1.11:1.51:0.38.

[Chem. 19]

(11-3)

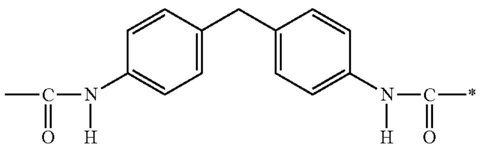

Herein, * designates a point of attachment to a hydroxyl group in another sugar unit.

Synthesis Example 3

To 15 g of hexamethylene diisocyanate, 48.1 g of a compound having the following general formula (12) was added. Reaction was carried out at 70° C. for 1 hour, obtaining 63.0 g of a prepolymer having the following general formula (13).

[Chem. 20]

(12)

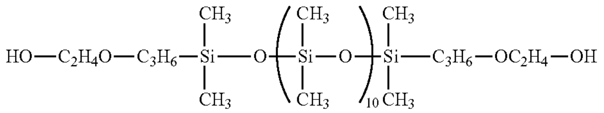

(13)

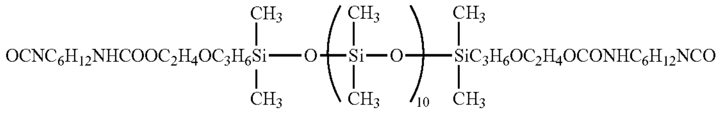

After 6 g of γ-cyclodextrin which had been dried at 110° C. for 2 hours and 100 g of N-methylpyrrolidone were dissolved by heating at 80° C., 0.5 g of triethylamine and 6.3 g of the prepolymer having formula (13) were added. The solution was stirred at 100° C. for 3 hours for reaction. Thereafter, 25.3 g of isocyanate-containing organopolysiloxane having formula (10) was added dropwise.

The solution was stirred at 110° C. for 3 hours for reaction. With stirring, the reaction solution was added to 500 g of water. The resulting precipitate was collected by filtration, washed twice with 300 g of water, and further twice with 300 g of a 1/1 (weight ratio) water/methanol mixture. On drying, 32.0 g of white solid was obtained (yield 85%). It was analyzed for substitution molar ratio of hydroxyl group by $^{1}$H-NMR spectroscopy. There was obtained an organopolysiloxane-modified cyclodextrin compound in which for R in the sugar unit having formula (11), the ratio of hydrogen:monovalent group having formula (11-1): divalent group having the following formula (11-4) is 1.46:1.43:0.11.

[Chem. 21]

(11-4)

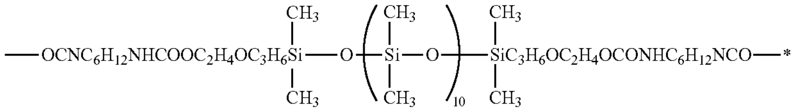

Herein, * designates a point of attachment to a hydroxyl group in another sugar unit.

Synthesis Example 4

After 6 g of γ-cyclodextrin which had been dried at 110° C. for 2 hours and 100 g of N-methylpyrrolidone were dissolved by heating at 80° C., 0.5 g of triethylamine and 18.9 g of the prepolymer having formula (13) were added. The solution was stirred at 100° C. for 3 hours for reaction. Thereafter, 7.2 g of isocyanate-containing organopolysiloxane having formula (10) was added dropwise.

The solution was stirred at 110° C. for 3 hours for reaction. With stirring, the reaction solution was added to 500 g of water. The resulting precipitate was collected by filtration, washed twice with 300 g of water, and further twice with 300 g of a 1/1 (weight ratio) water/methanol mixture. On drying, 26 g of white solid was obtained (yield 81.0%). It was analyzed for substitution molar ratio of hydroxyl group by $^{1}$H-NMR spectroscopy. There was obtained an organopolysiloxane-modified cyclodextrin compound in which for R in the sugar unit having formula (11), the ratio of hydrogen:monovalent group having formula (11-1): divalent group having formula (11-4) is 2.20:0.45:0.35.

Synthesis Example 5

After 10 g of α-cyclodextrin which had been dried at 110° C. for 2 hours and 120 g of N-methylpyrrolidone were dissolved by heating at 80° C., 0.5 g of triethylamine and 3.85 g of 4,4'-diphenylmethane diisocyanate were added. The solution was stirred at 100° C. for 3 hours for reaction. Thereafter, 17.4 g of isocyanate-containing organopolysiloxane having the general formula (14) was added dropwise.

[Chem. 22]

(14)

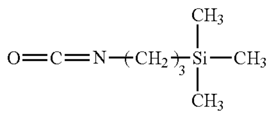

The solution was stirred at 110° C. for 3 hours for reaction. With stirring, the reaction solution was added to 500 g of water. The resulting precipitate was collected by filtration, washed twice with 300 g of water, and further twice with 300 g of a 1/1 (weight ratio) water/methanol mixture. On drying, 25.7 g of white solid was obtained (yield 82.3%). It was analyzed for substitution molar ratio of hydroxyl group by $^{1}$H-NMR spectroscopy. There was obtained an organopolysiloxane-modified cyclodextrin compound in which for R in the sugar unit having the following formula (11), the ratio of hydrogen:monovalent group having the following formula (11-5): divalent group having formula (11-3) is 1.06:1.71:0.23.

[Chem. 23]

(11-5)

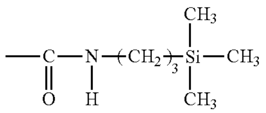

Comparative Synthesis Example 1

After 10 g of γ-cyclodextrin which had been dried at 110° C. for 2 hours and 120 g of N-methylpyrrolidone were dissolved by heating at 80° C., 0.5 g of triethylamine was added. Thereafter, 29.2 g of isocyanate-containing organopolysiloxane having formula (10) was added dropwise.

The solution was stirred at 110° C. for 3 hours for reaction. With stirring, the reaction solution was added to 500 g of water. The resulting precipitate was collected by filtration, washed twice with 300 g of water, and further twice with 300 g of a 1/1 (weight ratio) water/methanol mixture. On drying, 34.2 g of white solid was obtained (yield 85.1%). It was analyzed for substitution molar ratio of hydroxyl group by $^1$H-NMR spectroscopy. There was obtained an organopolysiloxane-modified cyclodextrin compound in which for R in the sugar unit having the following formula (11), the ratio of hydrogen to monovalent group having formula (11-2) is 1.90:1.10.

Comparative Synthesis Example 2

After 6 g of γ-cyclodextrin which had been dried at 110° C. for 2 hours and 100 g of N-methylpyrrolidone were dissolved by heating at 80° C., 0.5 g of triethylamine and 30.2 g of the prepolymer having formula (13) were added. The solution was stirred at 100° C. for 3 hours for reaction. With stirring, the reaction solution was added to 500 g of water. The resulting precipitate was collected by filtration, washed twice with 300 g of water, and further twice with 300 g of a 1/1 (weight ratio) water/methanol mixture. On drying, 36.7 g of white solid was obtained (yield 84.5%). It was analyzed for substitution molar ratio of hydroxyl group by $^1$H-NMR spectroscopy. There was obtained an organopolysiloxane-modified cyclodextrin compound in which for R in the sugar unit having formula (11), the ratio of hydrogen to divalent group having formula (11-4) is 2.49:0.51.

Each of the organopolysiloxane-modified cyclodextrin compounds obtained in Synthesis Examples 1 to 5 and Comparative Synthesis Examples 1 and 2 was blended with decamethylcyclopentanesiloxane or isododecane in a concentration of 10% by weight. The blend was stirred at 100° C. for 3 hours, after which it was visually observed at room temperature. Gelation or viscosity buildup was shown in Table 1.

TABLE 1

| Organopolysiloxane-modified | | Synthesis Example | | | | | Comparative Synthesis Example | |
|---|---|---|---|---|---|---|---|---|
| cyclodextrin compound | | 1 | 2 | 3 | 4 | 5 | 1 | 2 |
| Molar ratio ($N_H$) of hydrogen | | 1.61 | 1.11 | 1.46 | 2.20 | 1.06 | 1.90 | 2.49 |
| Molar ratio ($N_S$) of R derived from isocyanate siloxane | | 1.15 | 1.51 | 1.43 | 0.45 | 1.71 | 1.10 | — |
| Molar ratio ($N_L$) of R derived from diisocyanate | | 0.24 | 0.38 | 0.11 | 0.35 | 0.23 | — | 0.51 |
| Gelation | Decamethyl cyclopentasiloxane | gelled | gelled | gelled | gelled | gelled | dissolved | insoluble |
| | Isododecane | gelled | gelled | gelled | gelled | gelled | dissolved | insoluble |

All the compounds of Synthesis Examples 1 to 5 were dissolved at 100° C. and lost flow and gelled at room temperature. After the compound of Comparative Synthesis Example 1 was dissolved at 100° C., it remained dissolved without gelation at room temperature. The compound of Comparative Synthesis Example 2 was not dissolved at 100° C. and remained undissolved at room temperature.

Examples and Comparative Examples (Stability Evaluation)

Components (1), (3), (4) to (9) were mixed into a uniform dispersion, after which component (2) was gradually added and mixed. A solution of components (10) and (11) in (12) was moderately added to the mixture and emulsified, obtaining water-in-oil emulsion of the composition shown in Table 2. A glass bottle was filled with the W/O emulsion and held at 50° C. for 7 days during which the age stability of the emulsion was evaluated by visually observing the outer appearance and a viscosity change from the initial. It is noted that the viscosity was measured at 25° C. by a BM viscometer (Toki Sangyo Co., Ltd., rotor No. 3 or No. 4, 30 rpm, 1 min). The blending amount in Table 2 is the amount of the designated product blended (the same, hereinafter).

TABLE 2

| | Composition (%) | | Example 1 | Example 2 | Example 3 | Example 4 | Comparative Example 1 | Comparative Example 2 | Comparative Example 3 |
|---|---|---|---|---|---|---|---|---|---|
| 1 | Polyether-modified silicone (*1) | | 2 | 2 | 2 | 2 | 2 | 2 | 2 |
| 2 | Dimethylpolysiloxane (*2) | | 18 | 18 | 18 | 18 | 18 | 18 | 18 |
| 3 | Decamethylcyclopentasiloxane | | 2 | 2 | 2 | 2 | 2.5 | 2 | 2 |
| 4 | Compound of Synthesis Example 1 | | 0.5 | | | | | | |
| 5 | Compound of Synthesis Example 2 | | | 0.5 | | | | | |
| 6 | Compound of Synthesis Example 3 | | | | 0.5 | | | | |
| 7 | Compound of Synthesis Example 4 | | | | | 0.5 | | | |
| 8 | Compound of Comparative Synthesis Example 1 | | | | | | | 0.5 | |
| 9 | Compound of Comparative Synthesis Example 2 | | | | | | | | 0.5 |
| 10 | 1,3-butanediol | | 7 | 7 | 7 | 7 | 7 | 7 | 7 |
| 11 | Sodium chloride | | 0.5 | 0.5 | 0.5 | 0.5 | 0.5 | 0.5 | 0.5 |
| 12 | Water | | 70 | 70 | 70 | 70 | 70 | 70 | 70 |
| Total | | | 100.0 | 100.0 | 100.0 | 100.0 | 100.0 | 100.0 | 100.0 |
| Stability | Visual observation | | not separated | not separated | not separated | not separated | slightly separated | slightly separated | slightly separated |
| | Viscosity (mPa · s) | Initial | 6,300 | 13,200 | 16,200 | 15,300 | 2,740 | 2,980 | 3,020 |
| | | After 50° C./7 days | 6,100 | 12,800 | 15,500 | 15,000 | 1,320 | 1,440 | 1,250 |

(*1) KF-6017 (INCI: PEG-10 Dimethicone) by Shin-Etsu Chemical Co., Ltd.
(*2) KF-96A-6cs (INCI: Dimethicone) by Shin-Etsu Chemical Co., Ltd.

Examples 1 to 4 were improved in age stability as demonstrated by no separation of the emulsion and no viscosity change after holding at 50° C. for 7 days whereas Comparative Example 1 having no gelling agent added and Comparative Examples 2 and 3 using Comparative Synthesis Examples 1 and 2 were inferior in age stability as demonstrated by a low initial viscosity, observed separation of the emulsion, and a change to low viscosity. Shown below are Examples of the cosmetic composition comprising the inventive organopolysiloxane-modified cyclodextrin compound.

Example 5: W/O Emulsion

| (Components) | (pbw) |
|---|---|
| 1. Compound of Synthesis Example 1 | 2.0 |
| 2. Dimethylpolysiloxane (kinematic viscosity 6 $mm^2/s$) | 16.0 |
| 3. Decamethylcyclopentasiloxane | 18.8 |
| 4. Glyceryl trioctanoate | 5.0 |
| 5. Polyether-modified silicone (*3) | 3.0 |
| 6. 1,3-butanediol | 5.0 |
| 7. Preservative | 0.1 |
| 8. Fragrance | 0.1 |
| 9. Purified water | 50.0 |
| Total | 100.0 |

(*3) KF-6017 (INCI: PEG-10 Dimethicone) by Shin-Etsu Chemical Co., Ltd.

(Preparation Method)

An emulsion was obtained by a: mixing components 1, 3 and 5, dissolving at 80° C., adding components 2 and 4, agitating and mixing, and b: mixing components 6 to 9 uniformly, adding the mix to a, agitating and mixing.

(Results)

The emulsion thus obtained was a W/O emulsion which showed a dry feeling free of greasiness and stickiness, long lasting performance, and improved stability.

Example 6: W/O Cream

| (Components) | (pbw) |
|---|---|
| 1. Compound of Synthesis Example 3 | 0.5 |
| 2. Dimethylpolysiloxane (kinematic viscosity 6 $mm^2/s$) | 12.0 |
| 3. Crosslinked polyether-modified silicone (*4) | 2.0 |
| 4. Polyether-modified branched silicone (*5) | 0.5 |
| 5. Dipropylene glycol | 10.0 |
| 6. Sodium citrate | 0.2 |
| 7. Ethanol | 5.0 |
| 8. Preservative | 0.1 |
| 9. Fragrance | 0.1 |
| 10. Purified water | 69.6 |
| Total | 100.0 |

(*4) KSG-210 (INCI: Dimethicone/PEG-10/15 Crosspolymer) by Shin-Etsu Chemical Co., Ltd.
(*5) KF-6028 (INCI: PEG-9 Polydimethylsiloxyethyl Dimethicone) by Shin-Etsu Chemical Co., Ltd.

(Preparation Method)

An emulsion was obtained by a: mixing components 1, 2 and 3, dissolving at 80° C., adding component 3, agitating and mixing, and b: mixing components 5 to 10 uniformly, adding the mix to a, agitating and mixing.

(Results)

The emulsion thus obtained was a W/O cream which showed a dry feeling free of greasiness and stickiness, long lasting performance, and improved stability.

Example 7: W/O Cream Foundation

| (Components) | (pbw) |
|---|---|
| 1. Compound of Synthesis Example 3 | 1.0 |
| 2. Crosslinked polyether-modified silicone (*6) | 3.0 |
| 3. Polyether-modified silicone (*7) | 1.0 |
| 4. Dimethylpolysiloxane (kinematic viscosity 6 $mm^2/s$) | 3.0 |
| 5. Decamethylpentasiloxane | 9.0 |
| 6. Glyceryl trioctanoate | 5.0 |
| 7. Neopentylglycol dioctanoate | 2.0 |

-continued

| (Components) | (pbw) |
|---|---|
| 8. Spherical polymethylsilsesquioxane powder (*8) | 1.5 |
| 9. Polyglycerin alkyl co-modified branched silicone (*9) | 2.0 |
| 10. Silicone-treated titanium oxide (*10) | 6.9 |
| 11. Silicone-treated red iron oxide (*11) | 0.38 |
| 12. Silicone-treated yellow iron oxide (*12) | 0.6 |
| 13. Silicone-treated black iron oxide (*13) | 0.12 |
| 14. Pentylene glycol | 5.0 |
| 15. Sodium chloride | 0.5 |
| 16. Preservative | 0.1 |
| 17. Fragrance | 0.1 |
| 18. Purified water | 58.8 |
| Total | 100.0 |

(*6) KSG-210 (INCI: Dimethicone/PEG-10/15 Crosspolymer) by Shin-Etsu Chemical Co., Ltd.
(*7) KF-6017P (INCI: PEG-10 Dimethicone) by Shin-Etsu Chemical Co., Ltd.
(*8) KMP-590 (INCI: Polymethylsilsesquioxane) by Shin-Etsu Chemical Co., Ltd.
(*9) KF-6105 (INCI: Lauryl Polyglyceryl-3 Polyglyceryl-3 Polydimethylsiloxyethyl Dimethicone) by Shin-Etsu Chemical Co., Ltd.
(*10) KTP-09W (INCI: Titanium Dioxide, Aluminum Hydroxide, Triethoxysilylethyl Polydimethylsiloxyethyl Hexyl Dimethicone) by Shin-Etsu Chemical Co., Ltd.
(*11) KTP-09R (INCI: Iron Oxides, Triethoxysilylethyl Polydimethylsiloxyethyl Hexyl Dimethicone) by Shin-Etsu Chemical Co., Ltd.
(*12) KTP-09Y (INCI: Iron Oxides, Triethoxysilylethyl Polydimethylsiloxyethyl Hexyl Dimethicone) by Shin-Etsu Chemical Co., Ltd.
(*13) KTP-09B (INCI: Iron Oxides, Triethoxysilylethyl Polydimethylsiloxyethyl Hexyl Dimethicone) by Shin-Etsu Chemical Co., Ltd.

(Preparation Method)

A foundation was obtained by a: mixing components 1, 3, 4 and part of 5, dissolving at 80° C., adding component 3, 6 to 8, agitating and mixing, b: agitating and mixing components 9 to 13 and remainder of 5, c: mixing components 14 to 16 and 18 uniformly, d: adding c to a, agitating and mixing for emulsification, and e: adding component 17 and b to d, agitating and mixing.

(Results)

The cream foundation thus obtained was a W/O cream foundation which showed a dry feeling free of greasiness and stickiness, long lasting performance, and improved stability.

Example 8: Cream Eye Color

| (Components) | (pbw) |
|---|---|
| 1. Compound of Synthesis Example 4 | 2.0 |
| 2. Polyether-modified branched silicone (*14) | 2.0 |
| 3. Dimethylpolysiloxane (kinematic viscosity 6 $mm^2/s$) | 6.5 |
| 4. Decamethylpentasiloxane | 26.6 |
| 5. Triethyl hexanoin | 6.0 |
| 6. Organo-modified bentonite | 1.2 |
| 7. Acrylate/dimethylsilicone copolymer (*15) | 1.5 |
| 8. Triethoxycaprylsilane-treated pigment (*16) | 5.0 |
| 9. Dipropylene glycol | 5.0 |
| 10. Sodium citrate | 0.2 |
| 11. Preservative | 0.1 |
| 12. Fragrance | 0.1 |
| 13. Purified water | 43.8 |
| Total | 100.0 |

(*14) KF-6028 (INCI: PEG-9 Polydimethylsiloxyethyl Dimethicone) by Shin-Etsu Chemical Co., Ltd.
(*15) KP-575 (INCI: Acrylates/Ethylhexyl Acrylate/Dimethicone Methacrylate Copolymer) by Shin-Etsu Chemical Co., Ltd.
(*16) pigment treated with AES-3083 (INCI: Triethoxycaprylsilane) by Shin-Etsu Chemical Co., Ltd.

(Preparation Method)

A cream was obtained by a: mixing components 1, 2, part of 4, and 6, adding 3 and 5, agitating and mixing, b: agitating and mixing components 9 to 11 and 13, c: mixing components 7, 8 and remainder of 4 uniformly, d: adding b to a, agitating and mixing for emulsification, and e: adding component 12 and c to d, agitating and mixing.

(Results)

The cream eye color thus obtained was a cream eye color which showed a dry feeling free of greasiness and stickiness, long lasting performance, and improved stability.

Example 9: Sunscreen Cream

| (Components) | (pbw) |
|---|---|
| 1. Triethoxyalkylsilicone-treated zinc oxide (*17) | 20.0 |
| 2. Alkyl-polyglycerin co-modified silicone (*18) | 12.0 |
| 3. Decamethylcyclopentasiloxane | 20.0 |
| 4. Neopentylglycol dioctanoate | 8.0 |
| 5. Crosslinked alkyl-polyether co-modified silicone (*19) | 2.0 |
| 6. Compound of Synthesis Example 3 | 1.0 |
| 7. Alkyl-polyether co-modified silicone (*20) | 1.0 |
| 8. Octyl methoxycinnamate | 3.0 |
| 9. Sodium citrate | 0.2 |
| 10. Dipropylene glycol | 3.0 |
| 11. Preservative | 0.1 |
| 12. Fragrance | 0.1 |
| 13. Purified water | 29.6 |
| Total | 100.0 |

(*17) zinc oxide treated with KF-9909 (INCI: Triethoxysilylethyl Polydimethylsiloxyethyl Hexyl Dimethicone) by Shin-Etsu Chemical Co., Ltd.
(*18) KF-6105 (INCI: Lauryl Polyglyceryl-3 Polydimethylsiloxyethyl Dimethicone) by Shin-Etsu Chemical Co., Ltd.
(*19) KSG-310 (INCI: PEG-15/Lauryl Dimethicone Crosspolymer) by Shin-Etsu Chemical Co., Ltd.
(*20) KF-6038 (INCI: Lauryl PEG-9 Polydimethylsiloxyethyl Dimethicone) by Shin-Etsu Chemical Co., Ltd.

(Preparation Method)

A cream was obtained by a: heating part of component 3, and 4 to 8 at 80° C., agitating and mixing uniformly, b: mixing components 9 to 11 and 13, c: mixing components 1, 2 and remainder of 3, d: adding b to a, agitating and mixing for emulsification, and e: adding c and component 12 to (d), agitating and mixing.

(Results)

The cream thus obtained was a sunscreen cream which showed a dry feeling free of greasiness and stickiness, long lasting performance, and improved stability.

Example 10: Sunscreen Emulsion

| (Components) | (pbw) |
|---|---|
| 1. Crosslinked modified silicone (*21) | 4.0 |
| 2. Compound of Synthesis Example 2 | 1.0 |
| 3. Dimethylpolysiloxane (kinematic viscosity 6 $mm^2/s$) | 6.0 |
| 4. Glyceryl trioctanoate | 2.0 |
| 5. Polyether-modified silicone (*22) | 1.0 |
| 6. Titanium oxide/decamethyl-cyclopentasiloxane dispersion (*23) | 30.0 |
| 7. Zinc oxide/decamethyl-cyclopentasiloxane dispersion (*24) | 30.0 |
| 8. Dipropylene glycol | 3.0 |
| 9. Sodium citrate | 0.2 |

-continued

| (Components) | (pbw) |
|---|---|
| 10. Preservative | 0.1 |
| 11. Fragrance | 0.1 |
| 12. Purified water | 22.6 |
| Total | 100.0 |

(*21) KSG-15 (INCI: Dimethicone/Vinyl Dimethicone Crosspolymer) by Shin-Etsu Chemical Co., Ltd.
(*22) KF-6017 (INCI: PEG-10 Dimethicone) by Shin-Etsu Chemical Co., Ltd.
(*23) SPD-T5 (INCI: Cyclopentasiloxane, Titanium Dioxide, Polyglyceryl-3 Polydimethylsiloxyethyl Dimethicone, Aluminum Hydroxide, Stearic Acid) by Shin-Etsu Chemical Co., Ltd.
(*24) SPD-Z5 (INCI: Zinc Oxide, Cyclopentasiloxane, Titanium Dioxide, Polyglyceryl-3 Polydimethylsiloxyethyl Dimethicone) by Shin-Etsu Chemical Co., Ltd.

(Preparation Method)

A cream was obtained by a: agitating and mixing component 1 to 5 at 80° C., b: mixing components 8 to 10 and 12, c: adding b to a, agitating and mixing for emulsification, and d: adding component 6, 7 and 11 to c, agitating and mixing.

(Results)

The emulsion thus obtained was a sunscreen emulsion which showed a dry feeling free of greasiness and stickiness, long lasting performance, and improved stability.

It has been demonstrated that a cosmetic composition having the organopolysiloxane-modified cyclodextrin compound blended therein is free of greasiness and stickiness and shows a dry light feeling characteristic of silicone oil. When the cosmetic composition further contains pharmaceutical, fragrant and other components, they are formulated in a stable manner.

It is noted that the invention is not limited to the aforementioned embodiments. While the embodiments are merely exemplary, any embodiments having substantially the same construction as the technical concept set forth in the following claims and exerting equivalent functions and results are believed to be within the spirit and scope of the invention.

The invention claimed is:

1. An organopolysiloxane-modified cyclodextrin compound composed of sugar units having the formula (1):

[Chem. 1]

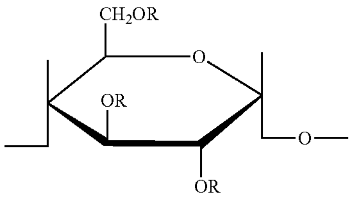

(1)

wherein R is independently hydrogen, a group having the formula (2):

[Chem. 2]

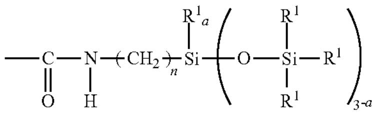

(2)

wherein $R^1$ is independently a group selected from among C1-C8 alkyl groups, C1-C8 fluorine-substituted alkyl groups, C6-C12 aryl groups, and C7-C12 aralkyl groups, n is an integer of 1 to 10, and a is an integer of 0 to 3, or a group having the formula (3):

[Chem. 3]

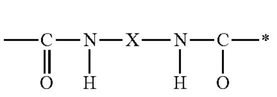

(3)

wherein X is a divalent organic group, and * is a point of attachment to a hydroxyl group of another sugar unit, wherein the ratio of the molar number $N_H$ of the hydrogen, the molar number $N_S$ of the group having formula (2), and the molar number $N_L$ of the group having formula (3) per mole of the organopolysiloxane-modified cyclodextrin compound is $N_H$:$N_S$:$N_L$=(0.5 to 2.5):(0.3 to 2.0):(0.1 to 0.5) and $N_H+N_S+N_L=3.0$.

2. The organopolysiloxane-modified cyclodextrin compound of claim 1 wherein X is a divalent organic group selected from C1-C10 divalent aliphatic hydrocarbon groups, C6-C20 divalent aromatic hydrocarbon groups, and groups having the formula (4):

[Chem. 4]

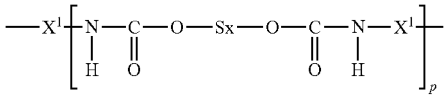

(4)

wherein $X^1$ is independently a C1-C10 divalent aliphatic hydrocarbon group or C6-C20 divalent aromatic hydrocarbon group, Sx is a divalent organopolysiloxane residue having the formula (5):

[Chem. 5]

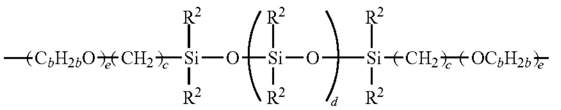

(5)

wherein $R^2$ is independently a group selected from among C1-C8 alkyl groups, C1-C8 fluorine-substituted alkyl groups, C6-C12 aryl groups, and C7-C12 aralkyl groups, b is independently a number of 2 to 4, c is independently an integer of 2 to 12, d is independently an integer of 0 to 200, e is independently a number of 0 to 40, and p is a number of 1 to 5.

3. The organopolysiloxane-modified cyclodextrin compound of claim 2 wherein X is a group selected from the following divalent hydrocarbon groups.

[Chem. 6]

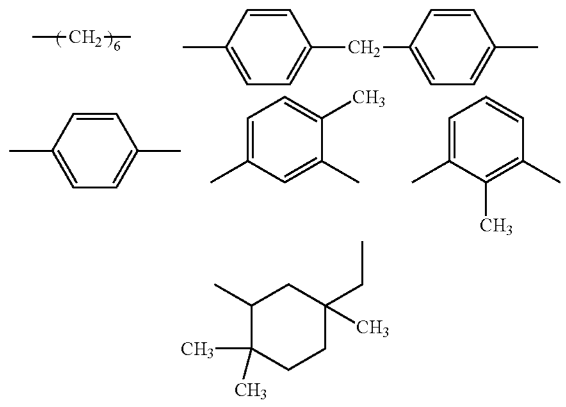

4. The organopolysiloxane-modified cyclodextrin compound of claim 1 wherein the sugar unit having formula (1) is derived from a cyclodextrin compound selected from α-cyclodextrin, β-cyclodextrin, γ-cyclodextrin, and derivatives of the foregoing cyclodextrins having a hydroxyethyl or hydroxypropyl group.

5. The organopolysiloxane-modified cyclodextrin compound of claim 1 wherein in formula (2), n=3 and $R^1$ is methyl.

6. A cosmetic composition comprising the organopolysiloxane-modified cyclodextrin compound of claim 1 in an amount of 0.05 to 20% by weight of the cosmetic composition.

7. The cosmetic composition of claim 6 further comprising water, the composition being in emulsion form.

8. The cosmetic composition of claim 6 further comprising at least one ingredient selected from silicone oils, hydrocarbon oils, ester oils, glyceride oils, and UV absorbers.

9. The cosmetic composition of claim 6 further comprising a powder, the composition being liquid, paste or solid.

* * * * *